(12) United States Patent
Litvin et al.

(10) Patent No.: US 8,483,360 B2
(45) Date of Patent: Jul. 9, 2013

(54) CORRECTION FOR SOURCE SWITCHING IN MULTI ENERGY SCANNER

(75) Inventors: Andrew Litvin, Wakefield, MA (US); Julia Pavlovich, Cambridge, MA (US); Aleksander Roshi, Medford, MA (US); Sergey Simanovsky, Brookline, MA (US); Ram Naidu, Newton, MA (US)

(73) Assignee: Analogic Corporation, Peabody, MA (US)

( * ) Notice: Subject to any disclaimer, the term of this patent is extended or adjusted under 35 U.S.C. 154(b) by 28 days.

(21) Appl. No.: 13/376,715

(22) PCT Filed: Jun. 12, 2009

(86) PCT No.: PCT/US2009/047180
§ 371 (c)(1),
(2), (4) Date: Dec. 7, 2011

(87) PCT Pub. No.: WO2010/144094
PCT Pub. Date: Dec. 16, 2010

(65) Prior Publication Data
US 2012/0087481 A1 Apr. 12, 2012

(51) Int. Cl.
*H05G 1/64* (2006.01)
*G06K 9/00* (2006.01)

(52) U.S. Cl.
USPC .................. 378/98.9; 378/4; 378/9; 382/130; 382/131

(58) Field of Classification Search
USPC .................. 378/4, 9, 98.9; 382/130
See application file for complete search history.

(56) References Cited

U.S. PATENT DOCUMENTS

| | | | | |
|---|---|---|---|---|
| 4,541,106 | A * | 9/1985 | Belanger et al. | 378/98.11 |
| 4,794,630 | A * | 12/1988 | Ploix | 378/98.12 |
| 6,507,633 | B1 | 1/2003 | Elbakri et al. | |
| 7,086,780 | B2 * | 8/2006 | Wu et al. | 378/207 |
| 7,489,762 | B2 * | 2/2009 | Bernhardt | 378/98.9 |
| 7,813,474 | B2 * | 10/2010 | Wu et al. | 378/16 |
| 7,949,088 | B2 * | 5/2011 | Nishide et al. | 378/5 |
| 8,165,264 | B2 * | 4/2012 | Zou | 378/5 |
| 8,199,874 | B2 * | 6/2012 | Toth et al. | 378/16 |

(Continued)

FOREIGN PATENT DOCUMENTS

| | | |
|---|---|---|
| EP | 1882449 | 1/2008 |
| WO | 9954754 | 10/1999 |
| WO | 2005009206 | 2/2005 |

OTHER PUBLICATIONS

International Search Report cited in related application No. PCT/US2009/047180 dated Sep. 11, 2009.

*Primary Examiner* — Alexander H Taningco
(74) *Attorney, Agent, or Firm* — Cooper Legal Group LLC

(57) ABSTRACT

The techniques described herein provide for correcting projection data that comprises contamination due to source switching in a multi energy scanner. The correction is a multi-neighbor correction. That is, it uses data from at least two other views of an object (e.g., generally a previous view and a subsequent view) to correct a current view of the object. The multi-neighbor correction may use one or more correction factors to determine how much data from the other two views to use to correct the current view. The correction factor(s) are determined based upon a calibration that utilizes image space data and/or projection space data of a phantom. In this way, the correction factor(s) account for source leakage that occurs in multi energy scanners.

20 Claims, 5 Drawing Sheets

U.S. PATENT DOCUMENTS 8,199,875 B2 * 6/2012 Chandra et al. .................. 378/16
8,311,182 B2 * 11/2012 Chandra et al. ................... 378/5
8,363,779 B2 * 1/2013 Chandra et al. .................. 378/16
2006/0109950 A1 5/2006 Arenson et al.

* cited by examiner

CORRECTION FOR SOURCE SWITCHING IN MULTI ENERGY SCANNER

BACKGROUND

The present application relates to the field of x-ray and computed tomography (CT). It finds particular application with dual-energy CT scanners. It also relates to medical, security, and other applications where obtaining information about the energy spectra of detected radiation would be useful.

CT and other radiographic imaging systems are useful to provide information, or images, of interior aspects of an object. Generally, the object is exposed to radiation, and an image is formed based upon the radiation absorbed by the interior aspects of the object, or rather an amount of radiation that is able to pass through the object. Typically, highly dense aspects of the object absorb more radiation than less dense aspects, and thus an aspect having a higher density, such as a bone or mass, for example, will be apparent when surrounded by less dense aspects, such as fat tissue or muscle. The detectors of a radiographic imaging system are configured to convert the radiographic energy that has traversed the object into signals and/or data that may be processed to produce images.

Multi energy imaging systems may be used to provide additional information about interior aspects of the object, beyond density, such as an atomic number. In particular, a dual energy imaging systems may be used for distinguishing between aspects of the object that have similar densities, such as white and grey brain matter, for example.

Multi energy imaging systems generally involve measuring the absorption characteristics of various aspects of the object for a plurality of energy spectra (e.g., a high energy spectrum and a low energy spectrum). While there are numerous ways to configure a multi energy imaging system for such measurement, one of the more common techniques is known as "source switching." Source switching is common because it allows for more discrimination between the radiation energy spectra (e.g., relative to techniques that utilize sandwich detectors), which may increase the accuracy of atomic number measurements, for example.

In source switching, the energy spectrum of the radiation is switched between at least two distinguished or different energy spectra. This may be done through a variety of procedures. In one procedure, the voltage applied to the radiation source is varied causing the emitted radiation's energy to vary with the change in voltage. In another procedure, two or more spatially separated sources are configured to alternate radiation emissions (e.g., by alternating power to the sources). Where there are two energy sources, for example, one of the sources may be configured to emit high energy spectrum radiation, while the other may be configured to emit low energy spectrum radiation.

None of the source switching procedures is ideal, however. For example, power to a radiation source cannot be switched on/off or varied instantaneously. Therefore, while the sources are switching the energy spectrum of the radiation, overlap between x-ray emissions may occur. Such overlap is hereafter referred to as source leakage (regardless of whether it results from a change in voltage applied to a single source, or from switching between multiple sources). The non ideal source switching may cause data contamination, by combining different energy spectrum radiation. The data contamination caused by non-ideal switching may result in image artifacts (e.g., bright and dark arcs) that diminish the image quality of the scan.

SUMMARY

Aspects of the present application address the above matters, and others. According to one aspect, an apparatus is provided. The apparatus comprises a correction component configured to apply a multi-neighbor correction to projection space data. The multi-neighbor correction corrects for source leakage from one or more radiation sources.

According to another aspect, a method is provided. The method comprises applying a multi-neighbor correction to projection space data acquired from a multi energy scanner.

According to yet another aspect, a method for correcting data in a multi energy scanner is provided. The method comprises receiving phantom projection space data and determining a correction factor based upon the phantom projection space data. The method also comprises using the correction factor to correct projection space data in view of multi-neighbor data related to an object.

FIGURES

The application is illustrated by way of example and not limitation in the figures of the accompanying drawings, in which like references indicate similar elements and in which.

DESCRIPTION

Figure 1:
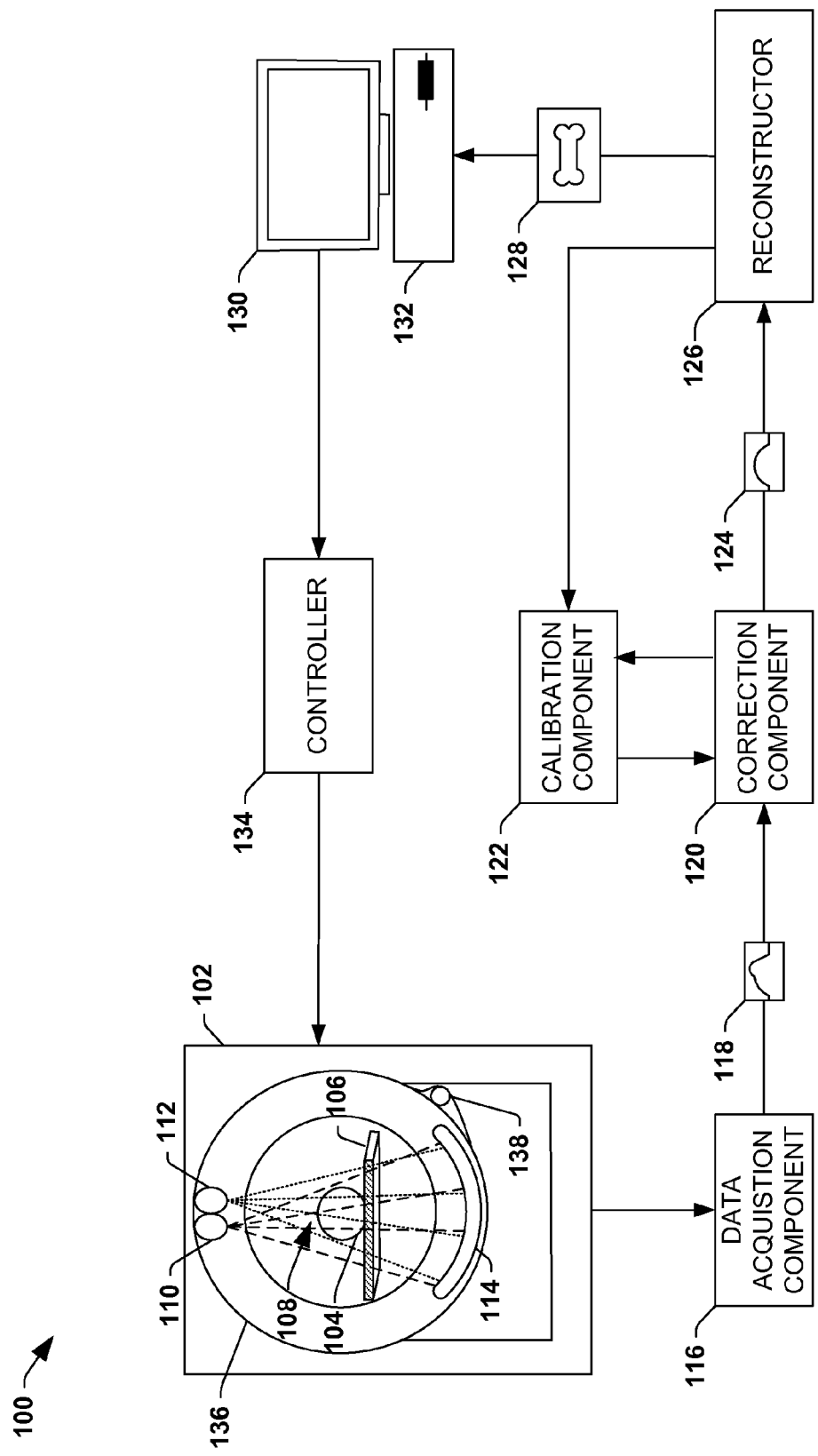
FIG. 1 is a schematic block diagram illustrating an example multi energy scanner.

FIG. 1 depicts an example multi energy scanner 100. Such a scanner 100 may be used in medical, security, and/or industrial applications, for example. One type of multi energy scanner is a dual energy computed tomography (CT) scanner. An object scanning apparatus 102 of the scanner 100 is configured to scan an object 104 under examination (e.g., a human patient, a piece of luggage, a package, etc.). The object 104 is generally placed on a surface 106, such as a bed or a conveyor belt, and selectively positioned in an examination region 108 of the object scanning apparatus 102. A bore-like rotating gantry 136 generally surrounds the examination region 108 and comprises a radiation source 110 (e.g., an ionizing x-ray source) and a detector array 114 (e.g., a multi-channel detector array) mounted on a substantially diametrically opposite side of the rotating gantry 136 relative to the radiation source 110. During an examination, the rotating gantry 136 is rotated by a motor 138, and the radiation source 110 emits fan, cone, wedge, and/or other shaped radiation onto the object 104.

The multi energy scanner 100 utilizes a technique known as source switching to intermittently switch the energy spectrum of radiation emitted from the radiation source(s). In the illustrated figure, two radiation sources 110 and 112 are used to switch the energy spectrum of the radiation. A first radiation source 110 may be configured to emit high energy radiation, and a second radiation source 112 may be configured to emit low energy radiation. By alternating radiation flux emitted by the radiation sources 110 or 112, for example, either high energy spectrum radiation or low energy spectrum radiation may be generated in an alternating manner.

Other source switching techniques not described herein but known to those skilled in the art are also contemplated. For example, in another source switching technique, the voltage supplied to a single radiation source is varied between two or more levels causing the radiation's energy spectrum to be varied concurrently with the change in voltage. In another example, the radiation source comprises a rotatable filter, wherein a first portion of the filter is configured to filter out low energy radiation and a second portion of the filter is configured to filter out high energy radiation. Depending upon which portion of the filter is positioned between the focal spot and the examination region, the source may emit either high or low energy radiation.

The emitted radiation is comprised of photons. Photons that traverse the object 104 are detected by the detector array 114. The size and/or shape of the detector array 114 may depend upon the shape of the emitted radiation (e.g., fan, wedge, etc.), but the detector generally extends in the transverse direction (e.g., towards the left and right edges of the page) and the longitudinal direction (e.g., into and out of the page). Internal aspects of the object 104 (e.g., masses, scar tissue, threat items, etc.) may cause various amounts of photons to traverse the object 104 (e.g., creating areas of high traversal and areas of low traversal within the object 104 under examination).

The detector array 114 is configured to generate (analog) signals/pulses, in response to detected photons within respective channel of the detector array 114. Respective pulses are indicative of characteristics of detected photons. These pulses may be transferred to a data acquisition component 116 that is in operable communication with the detector array 114. The data acquisition component 116 is configured to combine related pulses into a view to generate projection space data 118. For example, respective views may represent pulses related to photons detected by different detector channels within a predefined temporal range (e.g., 1 millisecond), or related to photons emitted while the radiation sources 110 and 112 and the detector array 114 were at a particular angle relative to the object 104. Stated differently, as the rotating gantry 136 rotates, each consecutive view represents a projection of the object under examination at the incrementally increasing view angle. Generally, each view is intended to represent merely those pulses generated based upon detected photons of a single energy spectrum. For example, a first view may comprise pulses generated from a first set of low energy photons, a second view may comprise pulses generated from a first set of high energy photons, a third view may comprise pulses generated from a second set of low energy photons, etc. If the energy spectrum of the emitted radiation is varied at a predetermined temporal interval (e.g., every 10 milliseconds), respective views may also represent pulses detected within the predetermined temporal interval.

The projection space data 118 is transferred to a correction component 120 that is configured to correct for source leakage. Source leakage generally refers to radiation detected concurrently from different sources during a period when two or more sources operating at different energy levels are switching (e.g., one source is increasing and another source is decreasing the flux of emitted radiation). Source leakage may also refer to radiation detected during a period when a single source varies the flux of emitted radiation. As used herein, source leakage is intended to cover both the scenario where two or more sources are switched and the scenario where a single source varies the flux of emitted radiation. Source leakage contaminates the projection space data for a given view because the view is representative of radiation having two or more energy spectrum (e.g., a fraction of the view is acquired when another source is operational) possibly emitted from different spatial locations (when two or more sources are used). The contamination is undesirable because it may cause artifacts to appear on an image that is produced during the reconstruction process. For example, the contamination may cause geometry mismatch if the pulses were detected at a time when the first radiation source 110, at a first position, was assumed to be emitting radiation when in fact some pulses originated from radiation emitted from the second radiation source 112, at a different position. Similarly, the contamination may cause a reconstructor 126 to mistakenly associate the pulses as being related to low energy photons when in fact they are related to high energy photons. In this way, the image produced may be different from the image that would have been produced had there been no source leakage.

A calibration component 122 may be configured to calibrate the correction component 120 using either phantom projection space data (e.g., received from the correction component 120), acquired from an examination of a phantom (e.g., an object with known shape and characteristics), or image space data (e.g., received from the reconstructor 126). In this way, when non-phantom objects are scanned, the projection space data may be corrected so that the effect of source leakage on the resulting image space data is reduced (e.g., relative to no correction), for example.

Corrected projection space data 124 from the correction component 120 may be transmitted to the reconstructor 126. The reconstructor 126 is configured to perform multi energy decomposition, and generate image space data 128 indicative of the object 104 under examination using a suitable analytical, iterative, and/or other reconstruction technique (e.g., tomosynthesis reconstruction).

The image space data 128 may be presented in human perceptible form on a monitor 130 for human observation. In one embodiment, the monitor 130 displays a user interface, and a computer 132, operably coupled to the monitor 130, is configured to receive human input. The received input may be transmitted to a controller 134 configured to generate instructions for the object scanning apparatus 102. For example, a package inspector viewing the image space data 128 on the monitor 130 may want to view a different section of the object, may thus instruct the surface 106 to move the object.

Figure 2:
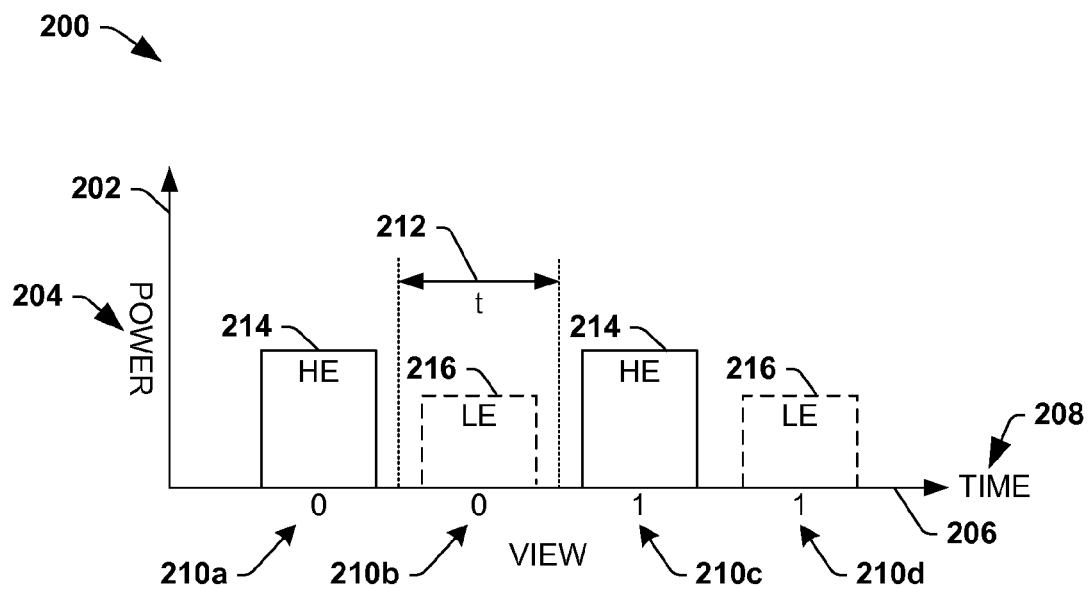
FIG. 2 illustrates a graph of radiation emission that would be generated if there were no source leakage.

FIG. 2 illustrates a graph 200 of radiation emissions that would be generated if there was ideal source switching (e.g., there was no source leakage). The y-axis 202 represents the power (e.g., voltage) 204 used in generating the radiation flux that is detected, and the x-axis 206 represents time 208 over which radiation flux is detected. Respective views 210a-210d are depicted in the illustrated example, where the different views represent intervals of time during which radiation having a given energy spectrum is detected. For example, during time interval "t" 212 radiation having a low energy spectrum, is detected. It will be appreciated that the time intervals during which energy is detected are longer than the "pulses" of radiation having a given energy spectrum (e.g., the time a source is driven at a corresponding voltage level) to capture the entirety of the radiation at the given energy spectrum (e.g., the more data that is collected, the better the resulting image).

In the illustrated example, the consecutive views at a given energy spectrum are indexed or numbered as 0, 1, 2, etc. In the illustrated example, however, the views from different energy spectra are interleaved, such that instead of appearing as 0, 1, 2, etc. on the x-axis, they instead appear or are sequenced as 0,0,1,1. It will be appreciated that this interleaving arrangement and the indexing or labeling thereof allows equations provided below to be developed to mitigate the effect of source leakage on resulting images. Accordingly, in the illustrated example, for each pair of interleaved views that have the same index (e.g., 0, 1, 2, etc.), the first view in the pair is coming from a first energy spectrum (e.g., the high energy (HE) source) and the second view is coming from a second energy spectrum (e.g., the low energy (LE) source), where the LE corresponds to a single source operated at a low voltage or one of multiple sources operated at a low voltage, and where the HE corresponds to the single source operated at a high voltage or one of multiple sources operated at a high voltage.

In an ideal environment there would not be source leakage because the radiation source(s) (e.g., 110 and 112 in FIG. 1) could power up and power down instantaneously. Therefore, the flux of the emitted radiation would increase/decrease instantaneously, and there would be no overlap in the data generated by the detection of high energy radiation 214 and data generated by the detection of low energy radiation 216. Respective views 210 would represent data related to radiation having a single energy spectrum. Unfortunately, energy sources cannot be powered up or down instantaneous (e.g., because of capacitance of the source(s) and/or power supply). Therefore, in practice, source switching is non-ideal.

Figure 3:
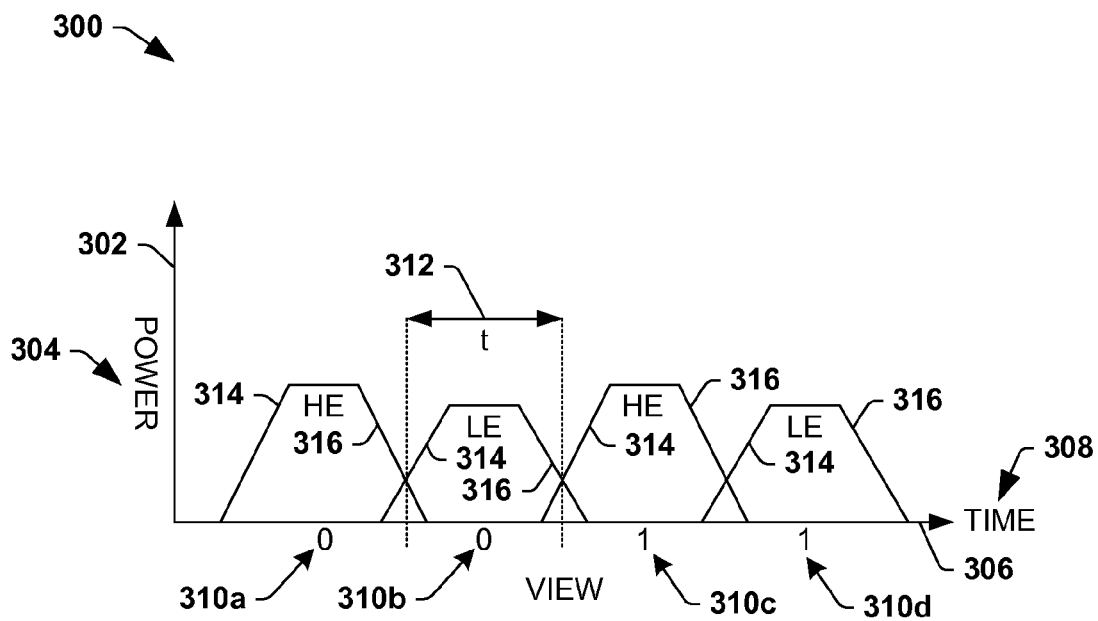
FIG. 3 illustrates a graph of radiation emission that is generated with source leakage.

FIG. 3 illustrates a graph 300 of radiation flux that is acquired when non-ideal source switching is present (e.g., there is source leakage). The y-axis 302 represents the power 304 associated with the emitted radiation flux and the x-axis 306 represents time 308. Respective views 310a-310d are depicted in the illustrated example, where the different views represent intervals of time during which radiation having a given energy spectrum is detected. For example, during time interval "t" 312 radiation having a low energy spectrum, is detected. As illustrated, the energy of emitted radiation gradually increases 314 as a source is powered up and gradually decreases 316 as a source is powered down. Therefore, respective views 310 comprise data related to detected radiation that does not correspond to a desirable (single) energy spectrum, and if multiple sources are used, may not correspond to radiation emitted from one source. It will be understood to those skilled in the art that it may be undesirable to reduce the time interval, t 312 of a view 310 (e.g., so that it just captures data representative of radiation at the correct energy spectrum) because it would decrease the amount of detected photons that could be used during the reconstruction process (e.g., degrading image quality).

Figure 4:
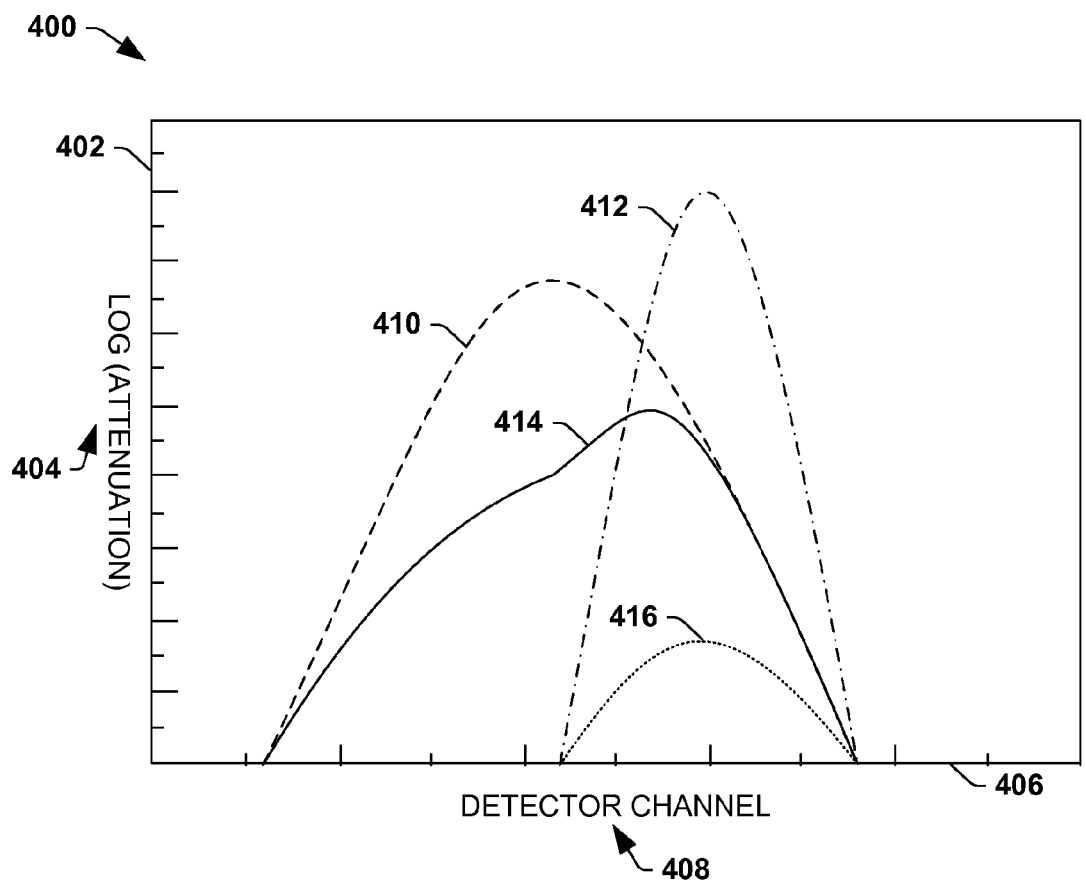
FIG. 4 illustrates a synthetic representation of projection space data related to a low energy view of a phantom that may be acquired in the presence of source leakage.

FIG. 4 illustrates a synthetic representation 400 of projection space data related to a low energy view of a phantom that may be acquired when source leakage is present. The y-axis 402 illustrates attenuation 404 of the radiation, or rather the log of attenuation, while the x-axis 406 represents detector channels 408 (e.g., spanning the detector array 114 in the transverse direction) that detect the photons. The figure is not to scale.

In an environment with ideal source switching, the view would substantially comprise data from low energy photons (e.g., represented by a dashed line 410) and would comprise little to no data from high energy photons. Due to non-ideal source switching (e.g., as illustrated in FIG. 3), the view also comprises data related to high energy photons (e.g., represented by a dash-dotted line 412). Therefore, the actual projection space data (e.g., illustrated by the solid line 414) comprises not only data from low energy photons, but also a contribution (e.g., represented by a dotted line 416) from high energy photons (emitted by a different source). This contribution may cause artifacts in an image generated from the projection space data.

Figure 5:
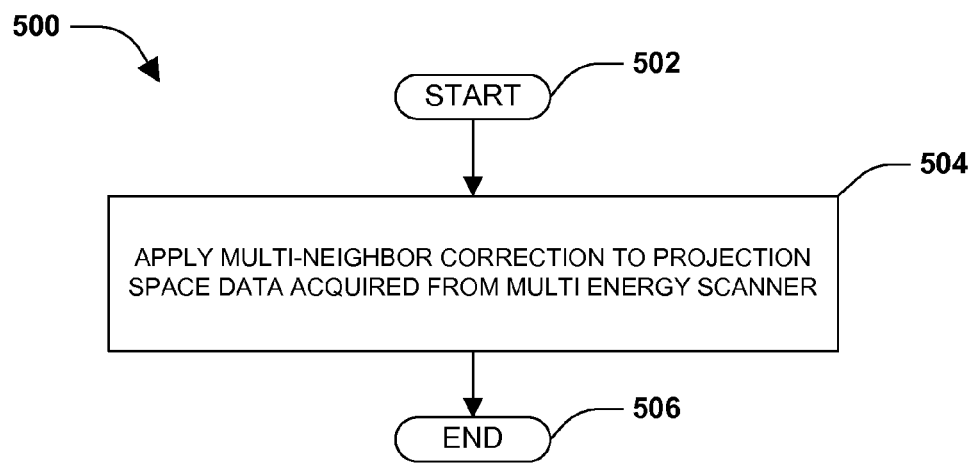
FIG. 5 is a flow diagram illustrating an example method for correcting for source leakage.

FIG. 5 illustrates a method 500 for correcting for source leakage. The method begins at 502, and a multi-neighbor correction is applied to data acquired from a radiation scanner at 504. The term multi-neighbor, as used herein refers broadly to a correction that involves comparing projection space data related to a current view of the object to projection space data related to at least two other views. Generally, the two other views comprise a view previous to the current view and a view subsequent to the current view.

The multi-neighbor correction corrects for contamination caused by source leakage. That is, the multi-neighbor correction may reduce the effect that the contribution from data related to high energy photons (e.g., as illustrated by dotted line 416 in FIG. 4) has on projection space data related to a low energy view and/or vise-versa, for example. In this way, the amount/severity of artifacts produced as a result of source leakage may be reduced.

In one embodiment, the multi-neighbor correction is applied by a correction component (e.g., 120 in FIG. 1) to projection space data (e.g., 118 in FIG. 1) received by a data acquisition component (e.g., 116 in FIG. 1). That is, the correction factor is used to correct projection space data in view of multi-neighbor data related to an object. The correction component generally uses projection space data from at least three views (e.g., a previous view, a current view, and a subsequent view) and applies the multi-neighbor correction to at least one of the views (e.g., the current view). For example, the correction component may acquire a previous high energy view, a current low energy view, and a subsequent high energy view. In this way, the correction component may subtract a portion of the data generated based upon detected high energy radiation in the previous and the subsequent views from the data in the low energy view (e.g., so that the remaining data is related to low energy radiation).

The projection space data is output by the data acquisition component in sequential temporal manner. That is, a first acquired view is output first, a second acquired view is output second, etc. Therefore, if the multi-neighbor correction is applied sequentially, the previous view may be already corrected while the subsequent view is uncorrected.

It will be understood by those skilled in the art that using an uncorrected subsequent view is sufficient for the method herein described because the correction generally represents a small fraction of the subsequent view's energy (e.g., on the order of 1-2%). That is, for most applications, using an uncorrected subsequent view to correct the current view is acceptable. Where it is unacceptable to use an uncorrected subsequent view, the method herein disclosed may be applied twice. That is, the multi-neighbor correction may be applied sequentially beginning at a first view and ending at view "n", where "n" is an integer greater than 0, and then the correction may be reversed, beginning at view "n" and ending at the first view. In this way, a current view may be corrected using both a corrected previous view and a corrected subsequent view.

At 506, the method ends.

Figure 6:
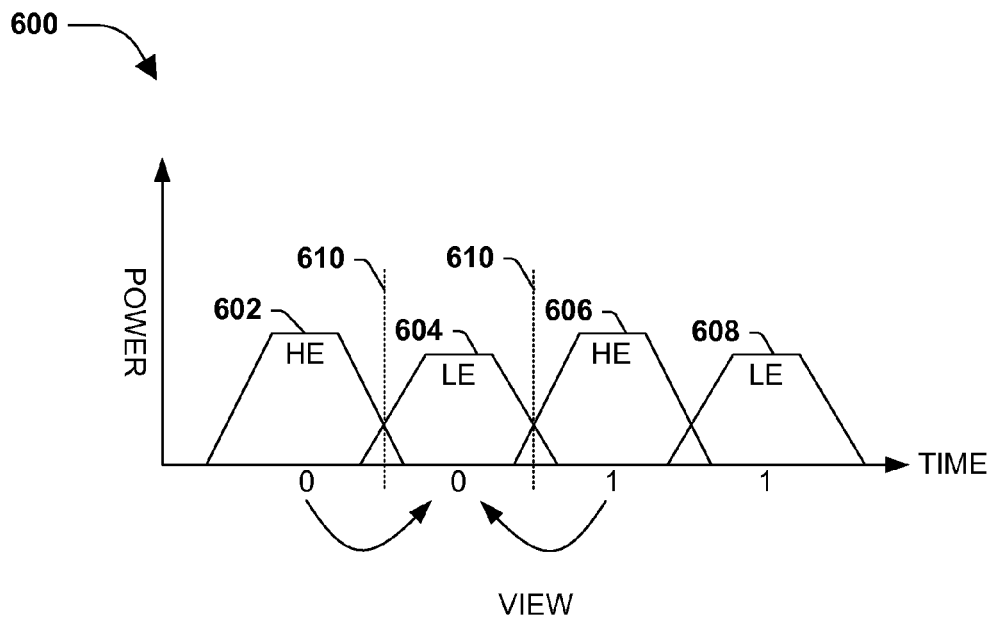
FIG. 6 illustrates a graphical representation of a multi-neighbor correction.

FIG. 6 is a graphical representation 600 of the multi-neighbor correction, wherein the data alternates between high energy views 602, 606 and low energy views 604, 608. The current view is the low energy view 604 (e.g., wherein dotted lines 610 identify the boundaries of the view). To correct the current low energy view 604, data related to the temporally previous high energy view 602 and to the temporally subsequent high energy view 606, may be multiplied by respective correction factors and subtracted from the current low energy view 604. In this way, a portion of the data related to the previous high energy view 602 and the subsequent high energy views are subtracted from the current low energy view. Once the current low energy view has been corrected, the correction component may begin to correct the next view (e.g., the subsequent high energy view 606 becomes the current view), for example. To correct the current high energy view 606, data related to the temporally previous low energy view 604, which has already been corrected, and to the temporally subsequent low energy view 608 may be multiplied by respective correction factors and subtracted from the current high energy view 606.

In one example, the multi-neighbor correction is as follows:

$$P_H^c[v]=P_H[v]+X_1P_L^c[v-1]+X_2P_L[v]$$

$$P_L^c[v]=P_L[v]+X_3P_H^c[v]+X_4P_H[v+1]$$

Where $P_H^c[v]$ and $P_L^c[v]$ are corrected high energy and low energy projections for respective views[v] and $X_1$, $X_2$, $X_3$, and $X_4$ are correction factors, respective factors representing a fraction of previous and subsequent views added to the current high energy or low energy view. In one embodiment the same correction factor may be used for $X_1, X_2, X_3$, and $X_4$.

Figure 7:
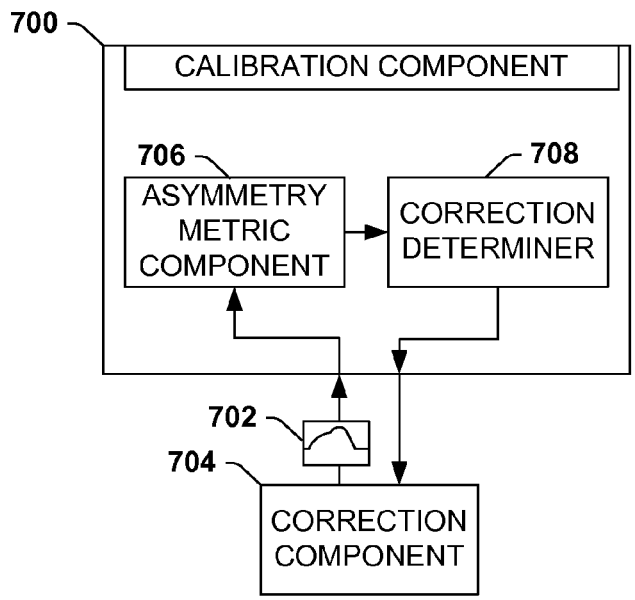
FIG. 7 illustrates an example calibration component.

FIG. 7 illustrates a first embodiment of a calibration component 700 (e.g., 122 in FIG. 1). The calibration component 700 is configured to receive phantom projection space data 702 (e.g., 118 in FIG. 1) related to a view of a phantom (e.g., an object with known configurations), such as a nylon cylinder, that is under examination by an object scanning apparatus (e.g., 102 in FIG. 1) and to determine one or more correction factors for a multi-neighbor correction. These correction factors may then be used by a correction component 704 (e.g., 120 in FIG. 1) to correct projection space data related to scanned objects with unknown configurations.

The calibration component 700 may comprise an asymmetry metric component 706 that is configured to receive the phantom projection space data 702. In the illustrated example, the phantom projection space data 702 is transmitted to the asymmetry metric component 706 from the correction component 704. However, other ways of transferring the phantom projection space data 702 to the asymmetry metric component 706 are contemplated. For example, the asymmetry metric component 706 may receive the phantom projection space data 702 from a data acquisition component (e.g., 116 in FIG. 1).

Using the phantom projection space data 702, the asymmetry metric component 706 determines the symmetry of the phantom projection space data 702 using techniques known to those skilled in the art (e.g., non-linear regression). If the object under examination is symmetrical, the phantom projection space data 702 should also be symmetrical (e.g., similar to the low energy projection space data represented by the dashed line 410 in FIG. 4). If the phantom is symmetrical, asymmetry in the phantom projection space data 702 is caused by source leakage. Therefore, by determining the asymmetry of the phantom projection space data 702 and determining corrections factors that cause the asymmetrical projection space data to become symmetrical, the calibration component 700 can instruct the correction component 704 how to correct for the source leakage, or rather how to correct for the asymmetry (e.g., through correction factors).

The calibration component 700 also comprises a correction determiner 708 configured to determine the correction factors based upon the symmetry, or rather asymmetry, of projection space data. That is, the correction determiner 708 determines values that would make the phantom projection space data 702 substantially symmetrical. These correction factors may then be transmitted to the correction component 704 so that future projection space data (e.g., related to scanned objects of unknown configurations) may be corrected using the multi-neighbor correction.

In one (of several different non-limiting) example(s), the correction determiner 708 uses the following acts to compute asymmetry metric and to determine the correction factors:

$$E(\overline{X})=\Sigma_{v=n_1}^{n_2}\Sigma_{i=i_1^v}^{i_2^v}(P_H^c[v,i]-P_H^c[v,i_1^v+i_2^v-i])^2+\Sigma_{v=n_1}^{n_2}\Sigma_{i=i_1^v}^{i_2^v}(P_L^c[v,i]-P_L^c[v,i_1^v+i_2^v-i])^2 \quad (1)$$

$$\overline{X}'=\overline{X}-s\nabla E(\overline{X}) \quad (2)$$

$$P_H^c[v,i]=P_H[v,i]+X'_1P_L^c[v-1,i]+X'_2P_L[v,i]P_L^c[v,i]=P_L[v,i]+X'_3P_H^c[v,i]+X'_4P_H[v+1,i] \quad (3)$$

Where $\overline{X}$ is a vector of correction factors, $E(\overline{X})$ is the asymmetry metric, $P_{H,L}^c[v,i]$ is a log-attenuation value for view v, detector index i; $n_1$ and $n_2$ are starting and ending view indices; $i_1^v$ and $i_2^v$ are the detector indices corresponding to the edges of the imaged object in the view v; $\overline{X}'$ is the updated vector of correction factors; $\nabla E(\overline{X})$ is the gradient of $E(\overline{X})$ with respect to correction factors in $\overline{X}$ and s is a step size.

In act (1), the asymmetry metric is computed as the norm of the difference between corrected projection and its copy reflected about the center. It can be appreciated by those skilled in the art that other methods to construct the metric can be employed (i.e. L1 norm). In act (2), the vector of correction factors $\overline{X}$ is updated by subtracting the gradient scaled by s from the current correction factors. The step size s may be kept constant or dynamically updated according to known step size management algorithms. The gradient $E(\overline{X})$ can be computed using a finite difference method. In act (3), the high ($P_H^c[v,i]$) and low ($P_L^c[v,i]$) energy projections are corrected in view of the updated correction factors $\overline{X}'$. Acts (1), (2), and (3) may be repeated until the correction factors in the vector $\overline{X}$ do not change by more than a specified minimum change.

In other embodiments, the calibration component 700 may use other components and/or other procedures to determine the correction factors. For example, if the phantom is not symmetrical, the projection space data would not be symmetrical, even without source leakage. Therefore, determining one or more correction factors that would make the projection space data substantially symmetrical would be incorrect. Instead, for example, a comparison of the actual projection space data for the phantom and the theoretical projection space data of the phantom may be used to determine the correction factors for the multi-neighbor correction. That is, the calibration component 700 may be configured to determine correction factors that cause the actual projection space data to fit the theoretical projection space data.

Figure 8:
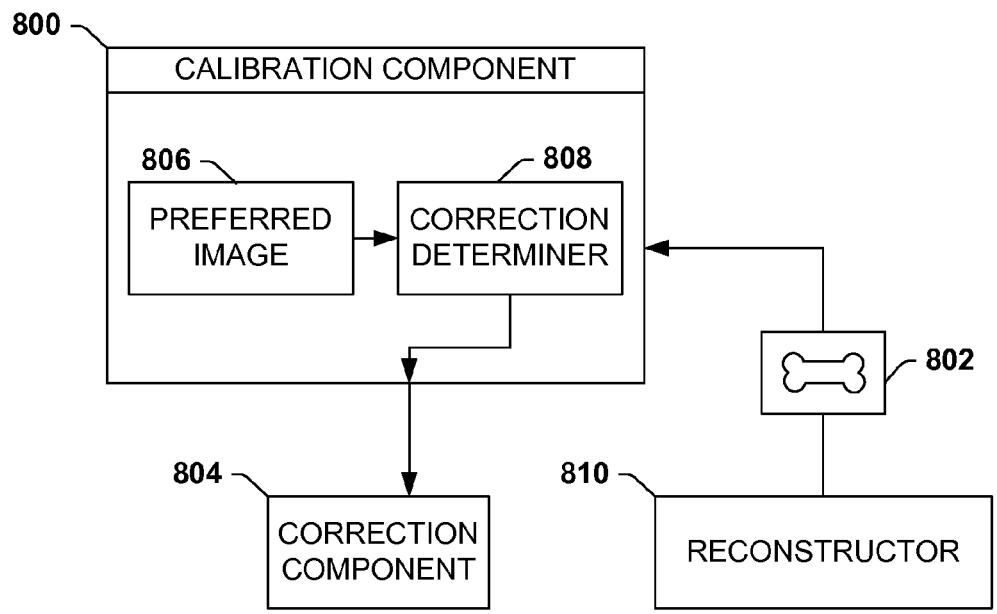
FIG. 8 illustrates an example calibration component.

FIG. 8 illustrates a second embodiment of a calibration component 800 (e.g., 122 in FIG. 1). The calibration component 800 is configured to receive image space data 802 (e.g., 128 in FIG. 1) related to an object (e.g., a phantom) with known configurations, such as a nylon cylinder, that is under examination by an object scanning apparatus (e.g., 102 in FIG. 1) and to determine one or more correction factors for a multi-neighbor correction. These correction factors may then be used by a correction component 804 (e.g., 120 in FIG. 1) to correct projection space data (e.g., 118 in FIG. 1) related to scanned objects with unknown configurations.

In the illustrated example, the calibration component 800 comprises a preferred image of the phantom 806 (e.g., an image of the phantom under ideal conditions) and a correction determiner 808 configured to compare the preferred image of the object 806 with the received image space data 802, produced from an examination of the object, to determine correction factors that reduce the effects of the artifacts. That is, the correction determiner 808 determines correction factors that, when applied to projection space data of the object, cause the received image space data 802 (e.g., reconstructed by a reconstructor 810) to substantially match (e.g., be nearly identical) the preferred image of the object 806. In this way, the correction determiner 808 determines how to reduce dark spots and/or darken light spots, for example, on the received image space data 802.

In one (of several different non-limiting) example(s), using a uniform image as the preferred image 806, the correction determiner 808 attempts to find such correction factors that render the received image space data 802 substantially uniform. In one embodiment, the correction determiner 808 uses the following acts to compute a uniformity metric to determine the correction factors:

$$E(\overline{X}) = STD(I) \quad (1)$$

$$\overline{X}' = \overline{X} - s\nabla E(\overline{X}) \quad (2)$$

$$P_H^c[v,i] = P_H[v,i] + X'_1 P_L^c[v-1,i] + X'_2 P_L[v,i] P_L^c[v,i] = P_L[v,i] + X'_3 P_H^c[v,i] + X'_4 P_H[v+1,i] \quad (3)$$

Where $\overline{X}$ is a vector of correction factors, $E(\overline{X})$ is the uniformity metric, $P_{H,L}^c[v,i]$ is a log-attenuation projection space data; $\overline{X}'$ is the updated vector of correction factors; $\nabla E(\overline{X})$ is the gradient of $E(\overline{X})$ with respect to correction factors in $\overline{X}$ and s is a step size.

In act (1), the uniformity metric is computed as the standard deviation of the density values over a phantom region. It can be appreciated by those skilled in the art that other methods to construct the metric can be employed (i.e. peak-to-peak variation). In act (2), the vector of correction factors $\overline{X}$ is updated by subtracting the gradient scaled by s from the current correction factors. The step size s may be kept constant or dynamically updated according to known step size management algorithms. The gradient $E(\overline{X})$ can be computed using a finite difference method. In act (3), the high ($P_H^c[v,i]$) and low ($P_L^c[v,i]$) energy projections are corrected in view of the updated correction factors $\overline{X}'$. Acts (1), (2), and (3) may be repeated until the correction factors in the vector $\overline{X}$ do not change by more than a specified minimum change.

The means for comparing the preferred image to the received image space data may require user input and/or may be fully automated. In one example, a user acts as the correction determiner 808, adjusting the correction factors to achieve a substantial match between the received image space data 802 and the preferred image. In another example, computer software is used to compare the images and adjust the correction factors until the received image space data 802 is substantially matched to the preferred image of the phantom 806.

In some instances the second embodiment of the calibration component (e.g., illustrated in FIG. 8) may be slower than the first embodiment (e.g., illustrated in FIG. 7) because the data has to be converted into image space data before a correction determiner can determine correction factors. Additionally, the reconstruction process can cause artifacts to be inserted into the image space data (e.g., artifacts not caused by source leaking). The correction determiner in the second embodiment, which calibrates based upon image space data, may correct for such artifacts. Unfortunately, this may cause convergence problems during the reconstruction process (e.g., causing more artifacts to appear in the image space data) of projection space data related to objects with unknown characteristics.

Figure 9:
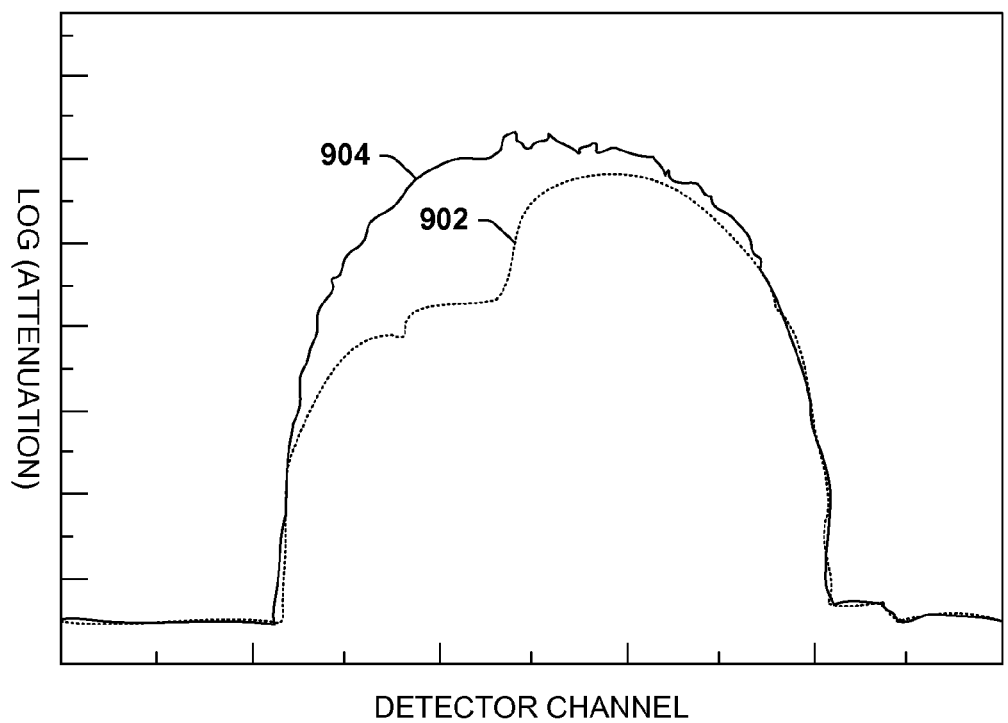
FIG. 9 illustrates uncorrected and corrected projection space data from a phantom object under examination.

FIG. 9 schematically illustrates data 900 from a phantom object under examination. More particularly, the figure illustrates projection space data related to a low energy view of a symmetrical phantom. The figure comprises both uncorrected projection space data 902 (e.g., represented by a dotted line) and corrected projection space data 904 (e.g., represented by a solid line). As illustrated, the uncorrected projection space data 902 is asymmetric (e.g., leaning leftward on the page) because of source switching. If the projection space data was not corrected, the image generated from the projection space data would have artifacts, potentially causing a portion of the object to be unviewable. However, after correction, the corrected projection space data 904 is substantially symmetrical, causing the resulting image to have substantially less artifacts.

It will be understood to those skilled in the art that there are numerous benefits to the apparatus and methods herein disclosed. For example, using a multi-neighbor correction substantially reduces the contamination caused by source switching. Additionally, calibration procedures may be done relatively quickly (e.g., between a few seconds and 20 minutes depending upon the procedure used) and may be done without significant human intervention. In this way, the techniques herein disclosed may provide a relatively cost effective and substantially error proof way of correcting for non-ideal source switching.

The application has been described with reference to various embodiments. Modifications and alterations will occur to others upon reading the application. It is intended that the invention be construed as including all such modifications and alterations, including insofar as they come within the scope of the appended claims and the equivalents thereof.

What is claimed is:

1. A multi-energy imaging apparatus, comprising:
a correction component configured to apply a multi-neighbor correction to projection space data indicative of detected radiation photons emitted from one or more radiation sources, the multi-neighbor correction configured to at least partially correct for source leakage from at least some of the one or more radiation sources.

2. The apparatus of claim 1, the multi-energy imaging apparatus comprising a dual-energy computed tomography (CT) scanner.

3. The apparatus of claim 1, comprising a calibration component configured to determine at least one correction factor for the multi-neighbor correction.

4. The apparatus of claim 3, the calibration component configured to determine the at least one correction factor based at least in part upon phantom projection space data.

5. The apparatus of claim 4, comprising an asymmetry metric component configured to determine a symmetry of the phantom projection space data.

6. The apparatus of claim 3, the calibration component configured to determine the at least one correction factor based at least in part upon image space data produced from an examination of an object.

7. The apparatus of claim 6, comprising a correction determiner configured to compare a preferred image of the object under examination to the image space data produced from the examination of the object.

8. The apparatus of claim 1, the correction component configured to receive projection space data related to a prior view, a current view, and a subsequent view of an object under examination.

9. The apparatus of claim 8, applying the multi-neighbor data correction comprising subtracting at least a portion of the received projection space data related to the prior view and at least a portion of the received projection space data related to the subsequent view from at least a portion of the received projection space data related to the current view.

10. The method of claim 1, applying the multi-neighbor correction to projection space data comprising:
applying the multi-neighbor correction to projection space data indicative of a current view, the multi-neighbor correction based at least in part upon projection space data indicative of a second view neighboring the current view, the current view intended to represent detected radiation photons emitted at a first energy spectrum and the second view intended to represent detected radiation photons emitted at a second energy spectrum, the second energy spectrum different than the first energy spectrum.

11. The method of claim 1, applying the multi-neighbor correction to projection space data comprising:
applying the multi-neighbor correction to projection space data indicative of a current view, the multi-neighbor correction based at least in part upon projection space data indicative of second and third views neighboring the current view, the current view intended to represent detected radiation photons emitted at a first energy spectrum, the second view intended to represent detected radiation photons emitted at a second energy spectrum, and the third view intended to represent detected radiation photons emitted at a third energy spectrum, the second and third energy spectra different than the first energy spectrum.

12. A method, comprising:
applying a multi-neighbor correction to projection space data acquired from a multi-energy scanner, the multi-neighbor correction configured to at least partially correct for contamination caused by source switching.

13. The method of claim 12, comprising:
receiving projection space data related to at least a prior view, a current view, and a subsequent view of an object under examination; and
applying the multi-neighbor correction comprising using at least a portion of the projection space data related to the prior view, the current view, and the subsequent view to correct projection space data related to the current view.

14. The method of claim 12, comprising determining a correction factor for the multi-neighbor correction based at least in part upon an examination of an object.

15. The method of claim 12, comprising:
detecting radiation that has traversed a phantom in an examination region of the scanner;
generating phantom projection space data based at least in part upon the detected radiation;
computing an asymmetry metric based at least in part upon the phantom projection space data; and
determining a correction factor for the multi-neighbor correction based at least in part upon the computed asymmetry metric.

16. The method of claim 12, comprising:
detecting radiation that has traversed an object in an examination region of the scanner;
generating projection space data based at least in part upon the detected radiation;
converting the projection space data into image space data;
comparing the image space data to a preferred image of the object under examination; and
determining a correction factor for the multi-neighbor correction based at least in part upon the comparison.

17. The method of claim 16, the correction factor configured to cause the image space data to substantially match the preferred image.

18. A method for correcting for contamination in data acquired via a multi-energy scanner, comprising:
receiving phantom projection space data;
determining a correction factor based at least in part upon the phantom projection space data; and
using the correction factor to correct projection space data in view of multi-neighbor data related to an object.

19. The method of claim 18, determining a correction factor, comprising:
computing an asymmetry metric based at least in part upon the phantom projection space data; and
determining a correction factor based at least in part upon the asymmetry metric.

20. The method of claim 18, before using, comprising receiving the projection space data related to the object, the received projection space data related to at least three views of the object.

* * * * *